United States Patent [19]

Spector

[11] Patent Number: 4,802,905

[45] Date of Patent: Feb. 7, 1989

[54] METHOD FOR PROTECTING PLANTS AND PLANT MATTER FROM STRESS

[75] Inventor: Marshall Spector, Emmaus, Pa.

[73] Assignee: Air Products and Chemicals, Inc., Allentown, Pa.

[21] Appl. No.: 24,273

[22] Filed: Mar. 10, 1987

[51] Int. Cl.$^4$ .................. A01N 3/02; A01N 33/04
[52] U.S. Cl. ........................... 71/68; 71/121
[58] Field of Search ................. 71/68, 121

[56] References Cited

U.S. PATENT DOCUMENTS

| | | | |
|---|---|---|---|
| 2,230,931 | 2/1941 | Bussert | 71/68 |
| 2,805,137 | 9/1957 | Clapton | 71/2.4 |
| 4,231,789 | 11/1980 | Okii et al. | 71/121 |

FOREIGN PATENT DOCUMENTS 0,239,296  6/1962  Australia .................. 514/673

OTHER PUBLICATIONS

Abeles, F. "Ethylene in Plant Biology", Academic Press, NY, 1973, Table of Contents.
A. Altman, R. Friedman, D. Amir & N. Levin, P. F. Warling ed: Plant Growth Substances, 1982, pp. 483–494.

Primary Examiner—Richard L. Raymond
Assistant Examiner—S. Treanor
Attorney, Agent, or Firm—Russell L. Brewer; James C. Simmons

[57] ABSTRACT

Crops, seeds, tissue cultures and cut flowers are protected from stress by application of polyamines and acid salts of such polyamines. The polyamines of this invention are represented by the general formula:

$$H_2NCHRCHR(-NHCHRCHR-)_nNH_2$$

where n represents an integer of from 1 to 3 and R represents either hydrogen or a methyl group.

9 Claims, No Drawings

METHOD FOR PROTECTING PLANTS AND PLANT MATTER FROM STRESS

FIELD OF THE INVENTION

The present invention relates to a method for prolonging the viability of plants by the application of polyamines to plants and plant matter.

BACKGROUND OF THE INVENTION

Plant life is susceptible to damage from stress associated with variations in temperature and moisture, injurious chemicals and combinations, and biological attack. Flowers, leaves, and other portions from plants which are cut also rapidly lose their fresh appearance due to the stress caused by such cutting. Substantial efforts have been made to extend the resistance of plants to stress associated with temperature and other causes as well as lengthen the shelf life of flowers, leaves, and other portions from plants. Representative patents which illustrate methods for conditioning plants and portions thereof for stress are as follows:

U.S. Pat. No. 2,805,137 discloses a process for conditioning cut flowers by applying an effective amount of a composition comprising a phenol, a compound selecting from the group consisting of carbonyl-containing compounds and compounds capable of being catabolized by plant enzymes to carbonyl-containing compounds and a compound selected from the group consisting of hydrazines, amines and quaternary ammonium compounds. Among the hydrazines and amines, which are alleged to have antiseptic properties and the ability to lower the surface tension of water and therefore suited for use are mono and diamines such as methylamine. ethylamine. diamines such as ethylene diamine, trimethylenediamine, and polyamines such as triamino methane. tetramethylene-tetramine and hexamethylene-tetramine. The phenol, is present in a proportion by weight of 5–1200 parts, the carbonyl-containing compound from 5,000 to 50,000 parts and the hydrazine or amine at a level from 10–900 parts.

U.S. Pat. No. 4,231,789 discloses the application of long chain polyamine compounds of the general formula $H_2N-R_1-NH_2$ wherein $R_1$ represents a $-(CH_2-)_n-$, where n represents an integer from 4–18 and various polyethylene polyamine amino derivatives thereof as a method for protecting crops from suffering various damages due to temperature, etc. Examples of suitable amines within the formula include tetramethylenediamine, pentamethylenediamine. hexadecamethylenediamine, spermidine an other polyamines. The polyamine is diluted to a concentration generally in the range of $10^{-4}$ to $10^{-2}$ moles per liter and applied as an aqueous formulation.

Naturally occurring polyamines have been widely reported to play a key role in protecting plants under a variety of stresses (Wareing, P.F. d: Plant Growth Substances, 1982, pp. 483–494, Academic Press). There is also an excellent review on the ability of naturally occurring polyamines to protect plants under a variety of stresses by "A. L. Galston (1983), Polyamines as Modulators of Plant Development. Bioscience, Volume 33 No. 6". Examples of natural polyamines tested and deemed suited for such use are: cadaverine (n-pentenediamine), putrescine (n-butylenediamine), spermidine (n-butylene/n-propylene triamine). and spermine (n-propylene/n-butylene/n-propylene tetramine.

U.S. Pat. No. 3,749,566 discloses a method for improving the resistance of rice seed to pre-emergence herbicides by applying an aqueous solution containing about 1% of sodium hypochloride bleaching solution and about 1/8th percent of a dimethylamine or diethanolamine salt of 1,8-napthalic anhydrid or acid.

SUMMARY OF THE INVENTION

This invention relates to a process for improving the resistance of plants to stress caused by extremes in temperature, extremes in moisture, physical trauma associated with cutting or associated with chemicals. The plants are protected by applying an effective amount of a polyamine, including salts thereof, of the formula:

$$H_2NCHRCHR(-NHCHRCHR-)_nNH_2$$

where n represents an integer from 1 to 3 and R represents either hydrogen or a methyl group to the plant. For ease of application the polyamine is dispersed in an inert carrier and applied in an amount sufficient to protect the plant and insufficient for effecting damage to such plant.

Significant advantages are achieved by the application of particular polyamines represented above to plants; these are:
- an ability to enhance protection of the plants to stress;
- an ability to protect plants from stresses at low molar concentrations; and;
- an ability to protect plants without inducing foliage spotting.

DETAILED DESCRIPTION OF THE INVENTION

Polyamine compositions represented by the formula above, which are suited for the practice of this invention and as a replacement in those instances where naturally occurring polyamines are used, are those polyamines which contain from 4 to 8 carbon atoms and include linear and branched alkylene polyamines. These polyamines in contrast to the naturally occurring polyamines have internal nitrogen atoms which are separated by 2 carbon atoms, i.e., an internal ethylene group. On the other hand, the naturally occurring polyamines of the prior art which were used to protect plants either had only external nitrogen atoms, or if internal nitrogen atoms were present, such internal nitrogen atoms were separated by more than 2 carbon atoms. Particular polyamines suited for practicing the invention are polyethylene polyamines such as diethylenetriamine (DETA), triethylene tetramine (TETA), and tetraethylene pentamine (TEPA). Other polyamines are polyisopropylene polyamines, poly 2-butene polyamines or mixtures of polyethylene/propylene or polybutene polyamines. Polyamine compounds having methyl substituents on one or both of the carbon atoms of the internal ethylene group are ethylene/isopropylene triamine, diisopropylene triamine, ethylene/2-butylene triamine.

The polyamines may also be employed as an amine salt and for purposes of this invention the amine salt is equivalent to and incorporated into the term polyamine. The conversion of naturally occurring amines to amine salt for application to plants is known and that technology is applicable to the utilization of the polyamines described here. Examples of amine salts include amine salts of both inorganic and organic acids and specific examples are amine acetates, amine propionates, amine hydrochlorides, amine sulfates, amine phosphates, and amine salts of napthalic acid and anhydride. From the above list then, there are diethylenetriamine acetate, chloride sulfate. etc.; and triethylene tetramine acetate, sulfate and napthenate.

The polyamine compositions are applied to the plants in amounts sufficient to exert or effect desired protection of the plant to the stress that may be anticipated and the amounts will vary based upon such stress and the type of plants to which the polyamine is administered. The polyamines are applied to the plants in conventional manner, e.g.. usually as a solution or a wettable powder. Broadly, the polyamines can be applied as an aqueous solution with the concentration of polyamine ranging from 0.01 to 20,000 micromolar, typically 1-2,000 micromolar. These solutions then are applied to the plant surface usually to the drip point to permit sorption of the amine into the plant. Generally, sorption levels range from $1 \times 10^{-5}$ to 1 micromols of polyamines per gram of fresh weight of plant. Apparently, because the polyamines have an internal ethylene group between nitrogen atoms, and therefore do not induce foliage spotting, substantial quantities of solution can be applied at variable exposure times without polyamine "burning."

The amount of active ingredient sorbed by a given plant is a function of the quantity of water sorbed by the plant, the concentration of polyamine in solution, the surface area of the plant exposed and the ease of transfer of the polyamine to the interior of the plant cells For example, seeds generally require more micromols of polyamine sorption per gram of fresh weight and are more impervious to polyamine sorption than leaves or cut flowers and may require treatment with the higher ranges of polyamine. In addition, longer exposure time and/or higher exposure temperatures may be called for. Therefore, while all of the polyamines of this invention are effective in stress protection, the straight moieties DETA, TETA and TEPA are preferred. However, it should be understood that the effectiveness of a given polyamine is in part intrinsic to the specific polyamine and that straightness of chain and molecular weight are not sole determinants of relative effectiveness in plant protection.

As is known from the art, the amount of polyamine to be applied for plant protection is different for different plants and different stresses. However, it is instructive to note that the amount of DETA calculated to protect an acre of soybeans against drought on the assumption (as in Example 1) of applying two milliliters of 1 micromolar DETA spray per plant, 2000 plants per acre and 10% spray efficiency is 4.1 grams.

The application of polyamines suited for use in the present invention is illustrated by the following examples:

EXAMPLE 1

Effect of Polyamines Under Drought

Twenty-five soybean plants were grown normally for 15 days prior to spraying to the drip point with an aqueous mist of various compositions using diethylenetriamine (DETA) as the test component and spermine as the control. Spermine was selected as the control polyamine because it appeared to be one of the best polyamines of the naturally occurring polyamines for the protection of plants. The plants were separated into 5 groups of 5 individual plants and each of the plants were sprayed with about two milliliters of aqueous solution applied as a mist which was sufficient to reach the drip point. The plants were then put out in a greenhouse and drought was simulated by not watering for 17 days. The temperature was maintained between about 20-25° C.

After 17 days of a first simulated "drought", the plants were watered to saturate the soil to full field capacity. Thereafter, all plants were again subJected to a second simulated drought and plants from each group were cut one inch above the soil level and tested for whole plant water potential (by the pressure bomb method) as a function of time in order to determine the ability of the plants to maintain a water potential more positive than minus 1.7 milliPascals (MPa). Plants with whole water potentials less positive than minus 1.7 MPa water potential are considered to be permanently wilted. Obviously, the longer a plant can survive before having a water potential more positive than minus 1.7 MPa, the more viable is the plant. The concentration of DETA and water potential times are shown in Table 1.

TABLE 1

Time to Water Potential of Minus 1.7 MPa

| Plant Group | Polyamine | Concentration of Polyamine | Time to Water Potential of Minus 1.7 MPa |
|---|---|---|---|
| 1 | Water (control) | Zero | 26 hours |
| 2 | DETA | 0.8 micromolar | 46 hours |
| 3 | DETA | 1.5 micromolar | 44 hours |
| 4 | DETA | 3.1 micromolar | 45 hours |
| 5 | DETA | 2000 micromolar | 36 hours |

Concentrations of 0.8, 1.5 and 3 micromolar were able to prolong the viability of soybeans under drought. The 2,000 micromolar spray was less effective than the lower concentrations.

Similar experimentation to that above was also performed with four groups of 5 soybean plants treated with spermine solution and the results are displayed in Table 2.

TABLE 2

| Plant Group | Concentration | Time to Water Potential of Minus 1.7 MPa |
|---|---|---|
| 1 | water spray | 24 hours |
| 2 | 1.5 micromolar spermine | 30 hours |
| 3 | 2000 micromolar spermine | 24 hours |
| 4 | 6000 micromolar spermine | 23 hours |

It is evident that the spermine was lends effective than DETA in all cases.

Even after 68 hours of second simulated exposure to drought, the remaining DETA treated plants appeared to be in good condition, while both water controls and the plant sprayed with 1.5 micromolar spermine appeared defunct. The appearance of the plant sprayed with 2000 micromolar spermine was equibalent to that of the plant sprayed with 1.5 micromolar DETA, but the plant sprayed with 6000 micromolar spermine evidenced polyamine burning.

EXAMPLE 2

"Polyamine Burning"

Three 15 day old soybean plants were sprayed with aqueous mists to the drip point in order to determine the effect of active component as compared to water on the plant. One plant was sprayed with a 2 millimolar DETA water solution one with a 2 millimolar Spermine solution and one with water. By the following day the spermine treated plant exhibited "polyamine burning,"

while the other two plants appeared normal. Thus, at equivalent molarity DETA solutions did not cause spotting while the naturally occurring polyamine, spermine, did cause such spotting.

EXAMPLE 3

Effect of Polyamines on Vase Life

Long stem Gerber daisies were selected for vase life tests because their heavy flowers tended to collapse on long delicate stems, thus providing a readily quantifiable vase life test. The water in the vase contained 0.2 grams of hydroxyquinone citrate and 20 grams of sucrose per liter. Each vase contained one flower and 200 mls of water or solution containing the test polyamine. The results are displayed in Table 3. The numbers represent the percent of acceptable stems on that day.

TABLE 3

| Day No. | Percent Acceptable Stems | | | | | | | | | | |
|---|---|---|---|---|---|---|---|---|---|---|---|
| | 1 | 2 | 3 | 4 | 5 | 6 | 7 | 8 | 9 | 10 | 11 |
| water | 100 | 100 | 100 | 100 | 100 | 100 | 57 | 57 | 43 | 29 | 0 |
| 200 micromolar Spermine | 100 | 100 | 100 | 86 | 86 | 86 | 86 | 71 | 57 | 43 | 0 |
| 400 micromolar Spermine | 100 | 100 | 100 | 100 | 86 | 71 | 71 | 76 | 71 | 71 | 0 |
| 800 micromolar Spermine | 100 | 100 | 100 | 100 | 100 | 86 | 57 | 29 | 14 | 0 | 0 |
| 1600 micromolar Spermine | 100 | 100 | 100 | 100 | 86 | 86 | 29 | 29 | 0 | 0 | 0 |
| water | 100 | 100 | 100 | 100 | 75 | 75 | 75 | 0 | 0 | 0 | 0 |
| 1 micromolar DETA | 100 | 100 | 100 | 100 | 100 | 100 | 100 | 75 | 75 | 50 | 25 |
| 10 micromolar DETA | 100 | 100 | 100 | 100 | 100 | 75 | 75 | 75 | 50 | 50 | 25 |
| 100 micromolar DETA | 100 | 100 | 100 | 100 | 100 | 100 | 75 | 75 | 50 | 50 | 25 |
| 1000 micromolar DETA | 100 | 100 | 100 | 100 | 100 | 100 | 100 | 75 | 75 | 75 | 50 |
| 1 micromolar TETA | 100 | 100 | 100 | 100 | 100 | 100 | 100 | 75 | 75 | 75 | 75 |
| 10 micromolar TETA | 100 | 100 | 100 | 100 | 100 | 100 | 75 | 75 | 50 | 25 | 25 |
| 100 micromolar TETA | 100 | 100 | 100 | 100 | 100 | 100 | 100 | 100 | 100 | 100 | 100 |
| 1000 millimolar TETA | 100 | 100 | 100 | 100 | 100 | 100 | 100 | 50 | 50 | 50 | 50 |

From the above data it is clear DETA and TETA were as effective as spermine in prolonging vase life of cut flowers at lower molar concentration than required for spermine or alternatively more effective at equivalent concentration. Some of the test candidates remained viable after 11 days even though the spermine and water-treated plants had wilted days before. Further, a higher percentage of the DETA and TETA treated plants remained viable much longer than the water and spermine treated plants. For example, after 6 days, the water and spermine treated plants began to deteriorate rapidly while the DETA and TETA plants deteriorated only slightly.

What is claimed:

1. In a process for protecting a plant from damage due to stress, wherein a polyamine or polyamine salt is applied to such plant in an amount effective for protecting such plant from stress, the improvement which comprises utilizing a polyamine represented by the formula $H_2NCHRCHR(-NHCHRCHR-)_nNH_2$ where n represents an integer of from 1 to 3 and R represents either hydrogen or a methyl group or a salt of such polyamine.

2. The process of claim 1 wherein the amine is applied to such plant as a aqueous solution.

3. The process of claim 1 further characterized in that said polyamine or polyamine salt is tetraetylene pentamine in an aqueous solution.

4. The process of claim 2 wherein the amine is present in the amount of from 0.01 to 20,000 micromolar.

5. The process of claim 4 wherein the solution is applied to foilage, seeds and cut flowers.

6. The process of claim 4 wherein the polyamine is diethylene triamine.

7. The process of claim 4 wherein said polyamine is triethylene tetramine.

8. The process of claim 4 wherein the polyamine is tetraethylene pentamine.

9. In a process for protecting a plant from damage due to stress, wherein a polyamine or polyamine salt is applied to such plant in an amount to provide a polyamine or polyamine salt sorption level of from $1 \times 10^{-5}$ to 1 micromole polyamine per gram of fresh weight of plant, the improvement which comprises utilizing diethylene triamine or salt thereof as said polyamine or polyamine salt.

* * * * *